US00RE48859E

(19) United States
(12) Reissued Patent
Guarr et al.

(10) Patent Number: US RE48,859 E
(45) Date of Reissued Patent: Dec. 21, 2021

(54) RECHARGEABLE LITHIUM-ION CELL

(71) Applicant: Board of Trustees of Michigan State University, East Lansing, MI (US)

(72) Inventors: Thomas F. Guarr, Holland, MI (US); Matthew M. Gregory, St. Joseph, MI (US); Nicholas Robert Boersma, Holland, MI (US); Robert Andrew Polik, Holland, MI (US); Nicholas Mortimer, Edwardsburg, MI (US)

(73) Assignee: Board of Trustees of Michigan State University, East Lansing, MI (US)

(21) Appl. No.: 16/592,326

(22) Filed: Oct. 3, 2019

Related U.S. Patent Documents

Reissue of:
(64) Patent No.: 10,249,910
Issued: Apr. 2, 2019
Appl. No.: 15/327,197
PCT Filed: Jul. 17, 2015
PCT No.: PCT/US2015/040970
§ 371 (c)(1),
(2) Date: Jan. 18, 2017
PCT Pub. No.: WO2016/011393
PCT Pub. Date: Jan. 21, 2016

U.S. Applications:
(60) Provisional application No. 62/026,212, filed on Jul. 18, 2014.

(51) Int. Cl.

| | |
|---|---|
| ***H01M 10/42*** | (2006.01) |
| ***C07D 209/86*** | (2006.01) |
| ***C07D 209/88*** | (2006.01) |
| ***C07D 241/46*** | (2006.01) |
| ***C07D 279/20*** | (2006.01) |
| ***C07D 279/22*** | (2006.01) |
| ***C07D 279/26*** | (2006.01) |
| ***H01M 10/0525*** | (2010.01) |
| ***H01M 10/0567*** | (2010.01) |
| ***H01M 10/0569*** | (2010.01) |

(52) U.S. Cl.
CPC ..... *H01M 10/4235* (2013.01); *C07D 209/86* (2013.01); *C07D 209/88* (2013.01); *C07D 241/46* (2013.01); *C07D 279/20* (2013.01); *C07D 279/22* (2013.01); *C07D 279/26* (2013.01); *H01M 10/0525* (2013.01); *H01M 10/0567* (2013.01); *H01M 10/0569* (2013.01)

(58) Field of Classification Search
CPC ..... H01M 10/4235; H01M 10/0525; H01M 10/0567; H01M 10/0569; H01M 4/62; C07D 209/86; C07D 209/88; C07D 241/46; C07D 279/20; C07D 279/22; C07D 279/26; Y02E 60/10
See application file for complete search history.

(56) References Cited

U.S. PATENT DOCUMENTS

| | | | | |
|---|---|---|---|---|
| 3,896,145 | A | 7/1975 | Berger et al. | |
| 5,976,731 | A | 11/1999 | Negoro et al. | |
| 6,249,369 | B1 | 6/2001 | Theiste et al. | |
| 6,445,486 | B1 | 9/2002 | Lomprey et al. | |
| 7,615,312 | B2 | 11/2009 | Dahn et al. | |
| 7,615,317 | B2 | 11/2009 | Dahn et al. | |
| 7,811,710 | B2 | 10/2010 | Dahn et al. | |
| 7,851,092 | B2 | 12/2010 | Amine et al. | |
| 8,367,253 | B2 | 2/2013 | Chen et al. | |
| 8,384,068 | B2 | 2/2013 | Kahle et al. | |
| 8,609,287 | B2 | 12/2013 | Zhang et al. | |
| 9,178,249 | B2 * | 11/2015 | Amine | H01M 10/0567 |
| 9,209,476 | B2 | 12/2015 | Knuckey et al. | |
| 2005/0221196 | A1 | 10/2005 | Dahn et al. | |
| 2006/0257746 | A1 * | 11/2006 | Inagaki | C01G 23/00 429/231.5 |
| 2006/0263697 | A1 | 11/2006 | Dahn et al. | |

(Continued)

FOREIGN PATENT DOCUMENTS

| | | | |
|---|---|---|---|
| CN | 101595591 | A | 12/2009 |
| EP | 0 827 230 | A2 | 3/1998 |

(Continued)

OTHER PUBLICATIONS

Non-Final Office Action (U.S. Appl. No. 16/462,419); dated Oct. 9, 2020; 20 pages.
Non-Final Office Action (U.S. Appl. No. 16/269,009); dated Nov. 24, 2020; 23 pages.
Examination Report No. 1 (AU Application No. 2018302335); dated Apr. 24, 2020; 9 pages.
Examination Report No. 2 (AU Application No. 2018302335); dated May 28, 2020; 3 pages.
Notice of Acceptance (AU Application No. 2018302335); dated Jul. 3, 2020; 3 pages.

(Continued)

*Primary Examiner* — Alan D Diamond
(74) *Attorney, Agent, or Firm* — Howard & Howard Attorneys PLLC

(57) ABSTRACT

A rechargeable lithium-ion cell has a cell capacity and includes a positive electrode having a recharged potential and a negative electrode. The rechargeable lithium-ion cell also includes a charge-carrying electrolyte. The charge-carrying electrolyte includes a charge-carrying medium and a lithium salt. The rechargeable lithium-ion cell also includes a redox shuttle having the following structure.

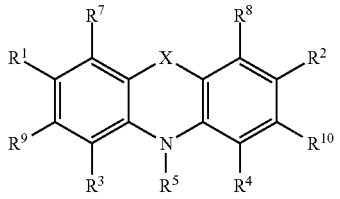

24 Claims, No Drawings

(56) References Cited

U.S. PATENT DOCUMENTS

| | | | | |
|---|---|---|---|---|
| 2007/0020479 | A1 | 1/2007 | Uetani et al. | |
| 2007/0196727 | A1 | 8/2007 | Wang et al. | |
| 2008/0014496 | A1 | 1/2008 | Watanabe et al. | |
| 2009/0042103 | A1 | 2/2009 | Xiao et al. | |
| 2010/0068621 | A1 | 3/2010 | Exnar et al. | |
| 2010/0187980 | A1 | 7/2010 | Langer et al. | |
| 2010/0297480 | A1 | 11/2010 | Martinent et al. | |
| 2011/0006738 | A1 | 1/2011 | Mikhaylik et al. | |
| 2011/0079773 | A1 | 4/2011 | Wasielewski et al. | |
| 2011/0244319 | A1* | 10/2011 | Hashimoto | H01M 2/021 429/186 |
| 2011/0294019 | A1 | 12/2011 | Amine et al. | |
| 2013/0288137 | A1 | 10/2013 | Weng et al. | |
| 2014/0178756 | A1 | 6/2014 | Ishii et al. | |
| 2015/0108451 | A1 | 4/2015 | Thompson et al. | |
| 2015/0248969 | A1 | 9/2015 | Watanabe et al. | |
| 2015/0372333 | A1 | 12/2015 | Odom et al. | |
| 2017/0062842 | A1 | 3/2017 | Huang et al. | |
| 2017/0162916 | A1 | 6/2017 | Guarr et al. | |
| 2019/0305381 | A1 | 10/2019 | Guarr et al. | |

FOREIGN PATENT DOCUMENTS

| | | | |
|---|---|---|---|
| EP | 827230 | * | 3/1998 |
| FR | 2866478 | A1 | 8/2005 |
| GB | 2507661 | A | 5/2014 |
| JP | H08195199 | A | 7/1996 |
| JP | H10134845 | A | 5/1998 |
| JP | H10144347 | A | 5/1998 |
| JP | 2001023687 | A | 1/2001 |
| JP | 2004101729 | A | 4/2004 |
| JP | 2007522628 | A | 8/2007 |
| JP | 2009272170 | A | 11/2009 |
| JP | 2012214671 | A | 11/2012 |
| JP | 2013501337 | A | 1/2013 |
| JP | 2015-086201 | A | 5/2015 |
| JP | 2015086202 | A | 5/2015 |
| JP | 2015115110 | A | 6/2015 |
| JP | 2016033117 | A | 3/2016 |
| JP | 2016-103417 | A | 6/2016 |
| WO | 99/09111 | A1 | 2/1999 |
| WO | 2009102604 | A1 | 8/2009 |
| WO | 2009/141288 | A2 | 11/2009 |
| WO | 2016011393 | A1 | 1/2016 |
| WO | 2018098116 | A2 | 5/2018 |
| WO | 2019018741 | A1 | 1/2019 |

OTHER PUBLICATIONS

Odom, Susan et al.; "Synthesis and analysis of redox shuttles for overcharge protection in lithium-ion batteries", 1 page.

Odom, Susan et al.; "Increasing redox shuttle oxidation potentials to match high voltage cathodes in lithium-ion batteries", 1 page, 2013.

Narayana, Klishore et al.; "N-substituted phenothiazine derivatives as electrolyte additives for overcharge protection in lithium-ion batteries", 1 page, 2014.

Ergun, Selin et al.; "Overcharge performance of 3,7-disubstituted N-ethylphenothiazine derivatives in lithium-ion batteries". The Royal Society of Chemistry, 3 pages, Nov. 11, 2013.

Odom, Susan et al.; "A fast, inexpensive method for predicting overcharge performance in lithium-ion batteries", The Royal Society of Chemistry, 8 pages, Nov. 11, 2013.

Narayana, Kishore Anand et al.; "N-Substituted Phenothiazine Derivatives: How the Stability of the Neutral and Radical Cation Forms Affects Overcharge Performance in Lithium-Ion Batteries", 11 pages, 2015.

Casselman, Matthew et al.; "The fate of phenothiazine-based redox shuttles in lithium-ion batteries", 8 pages, Jan. 22, 2015.

Kaur, Aman Preet et al.; "Overcharge protection of lithium-ion batteries above 4 V with a perfluorinated phenothiazine derivative", 5 pages, Mar. 10, 2016.

International Search Report and Written Opinion ; Office Action (PCT Application No. PCT/US2015/040970); dated Jan. 5, 2016; 19 pages.

International Search Report and Written Opinion; Office Action (PCT Appication No. PCT/US17/62698); dated Feb. 2, 2018; 9 pages.

Notification of Reasons for Refusal; Office Action (JP Application No. 2017-502961); dated Jun. 24, 2019; 9 pages.

International Search Report and Written Opinion; Office Action (PCT Application No. PCT/US18/43048); dated Sep. 17, 2018; 16 pages.

Adachi, Momoe et al., "Aromatic Compounds at Redox Shuttle Additives for 4 V Class Secondary Lithium Batteries" J. Electrochem. Soc. 1999, vol. 146(4)m pp. 1256-1261.

Sevov, Christo S. et al., "Physical Organic Approach to Persistent, Cyclable, Low-Potential Electrolytes for Flow Battery Applications", J. A,/ Chem Soc., vol. 139, No. 8, 2017, pp. 2924-2927.

English language abstract for JP2013501337 extracted from espacenet.com database on Jun. 17, 2021, 1 page.

English language abstract for JP2012214671 extracted from espacenet.com database on Jun. 17, 2021, 1 page.

English language abstract and machine-assisted English translation for JP2004101729 extracted from espacenet.com database on Jun. 17, 2021, 15 pages.

English language abstract and machine-assisted English translation for JP2015115110 extracted from espacenet.com database on Jun. 17, 2021, 32 pages.

English language abstract and machine-assisted English translation for JP2016033117 extracted from espacenet.com database on Jun. 17, 2021, 23 pages.

English language abstract and machine-assisted English translation for JPH08195199 extracted from espacenet.com database on Jun. 17, 2021, 12 pages.

International Search Report for Application No. PCT/US2015/040970 dated Jan. 5, 2016, 7 pages.

English language abstract for FR 2 866 478 extracted from espacenet.com database on Mar. 22, 2017, 1 page.

English language abstract for JPH 10-144347 extracted from espacenet.com database on Mar. 22, 2017, 1 page.

English language abstract and machine-assisted English translation for JP 2009-272170 extracted from espacenet.com database on Mar. 22, 2017, 19 pages.

Buhrmester, Claudia et al., "Phenothiazine Molecules-Possible Redox Shuttle Additives for Chemical Overcharge and Overdischarge Protection for Lithium-Ion Batteries", J. Electrochem. Soc., 2006, vol. 153(2), pp. A288-A294.

Zhang, Lu et al., "Lithium Ion Batteries—New Developments", Chapter 7—Redox Shuttle Additives for Lithium-Ion Battery, Chapter 7, Feb. 2012, pp. 173-188.

International Application No. PCT/US2018/043048 filed Jul. 20, 2018, 66 pages.

International Search Report for Application No. PCT/US2017/062698 dated Feb. 2, 2018, 1 page.

International Search Report for Application No. PCT/US2018/043048 dated Sep. 17, 2018, 1 page.

Sevov, Christo S. et al., "Physical Organic Approach to Persistent, Cyclable, Low-Potential Electrolytes for Flow Battery Applications", J. Am. Chem. Soc., vol. 139, No. 8, 2017, pp. 2924-2927.

Zhang, Lu et al., "Molecular Engineering Towards Safer Lithium-Ion Batteries: a Highly Stable and Compatible Redox Shuttle for Overcharge Protection", Energy Environ. Sci., vol. 5, 2012, pp. 8204-8207.

Zhang, Lu et al., "Novel Redox Shuttle Additive for High-Voltage Cathode Materials", Energy Environ. Sci., vol. 4, 2011, pp. 2858-2862.

English language abstract for CN101595591A extracted from espacenet.com dated Jan. 23, 2019, 1 page.

* cited by examiner

RECHARGEABLE LITHIUM-ION CELL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application *is a reissue of patent application Ser. No. 15/327,197, filed on Jan. 18, 2017, now U.S. Pat. No. 10,249,910 B2, which* is the National Stage of International Patent Application No. PCT/US2015/040970, filed on Jul. 17, 2015 which claims priority to and all the advantages of U.S. Provisional Patent Application No. 62/026,212, filed on Jul. 18, 2014, the content of which is incorporated herein by reference.

[CROSS-REFERENCE TO RELATED APPLICATIONS]

[The subject patent application claims priority to and all the benefits of U.S. Provisional Patent Application No. 62/026,212, filed on Jul. 18, 2014, the disclosure of which is herein incorporated by reference in its entirety.]

FIELD OF THE DISCLOSURE

The disclosure generally relates to a rechargeable lithium-ion cell. More specifically, this disclosure relates to a lithium-ion cell that includes a particular redox shuttle.

BACKGROUND

Rechargeable lithium-ion cells can exhibit excellent charge-discharge cycle life, little or no memory effect, and high specific and volumetric energy. However, lithium-ion cells typically exhibit an inability to tolerate recharging to potentials above the manufacturer's recommended end of charge potential without degradation in cycle life. Recharging to potentials above the manufacturer's recommended end of charge potential is typically described as overcharge. Overcharge generally occurs when a current is forced through the cells and the charge delivered exceeds the charge-storing capability of the cell. Overcharge of lithium-ion cells can lead to the chemical and electrochemical degradation of cell components, rapid temperature elevation, and can also trigger self-accelerating reactions in the cells.

To combat these problems, redox shuttles have been used. Redox shuttles are chemical compounds that are incorporated into lithium-ion cells for overcharge protection. Generally, the redox shuttle can be reversibly electrochemically oxidized at a potential slightly higher than the working potential of a positive electrode of the lithium-ion cell. Use of the redox shuttles allows lithium-ion cells to normally operate in a voltage range less than the redox potential of the redox shuttle. If the lithium-ion cells are charged to a level that exceeds their normal cell capacity (i.e., are "overcharged"), the voltage will increase to the redox potential of the redox shuttle first and activate a redox mechanism, which will proceed as the only active component to transfer the excessive charge through the lithium-ion cells while minimizing damage. Use of such a mechanism inhibits overcharging.

Research and development has identified various options for redox shuttles. However, identifying shuttle candidates having both a suitably high redox potential and a sufficient service life has proven difficult. Many redox shuttles tend to chemically degrade over time or impede normal cell operation, thereby becoming useless. Accordingly, there remains opportunity for improvement.

SUMMARY OF THE DISCLOSURE

This disclosure provides a rechargeable lithium-ion cell having a cell capacity and including a positive electrode having a recharged potential and a negative electrode. The rechargeable lithium-ion cell also includes a charge-carrying electrolyte. The charge-carrying electrolyte includes a charge-carrying medium and a lithium salt. In addition to the above, the rechargeable lithium-ion cell also includes a redox shuttle having the following structure:

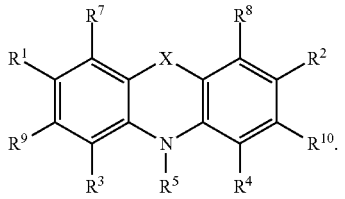

In this structure, X is a covalent bond (such that the center ring is a five membered ring), a sulfur atom (S), or a nitrogen atom bonded to $R^6$ (N—$R^6$). Moreover, each of $R^1$, $R^2$, $R^3$, $R^4$, $R^5$, $R^6$, $R^7$, $R^8$, $R^9$ and $R^{10}$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, [an oxo group,] an alkyl ether group, a trialkylammoniumalkyl group, a phosphate group, a phosphonate group, or an alkyl phosphonate group, and wherein one of $R^3$ and $R^4$ is optionally a hydrogen atom.

DETAILED DESCRIPTION OF THE DISCLOSURE

This disclosure provides a rechargeable lithium-ion cell (hereinafter described as the "cell".) The cell can be alternatively described as a battery, i.e., a rechargeable lithium-ion cell battery. The cell has a cell capacity, which is known in the art as an amount of electric charge the cell can deliver at a rated voltage. Typically, smaller cells have less cell capacity than larger cells of the same chemistry even though they can develop the same open-circuit voltage. Cell capacity is typically measured in units such as amp-hour (A·h). The capacity of the cell is often expressed as a product of 20 hours multiplied by the current that a new battery can consistently supply for 20 hours at 68° F. (20° C.), while remaining above a specified terminal voltage per cell. The capacity of the instant cell is not particularly limited and may be chosen by one of skill in the art.

The cell may be sealed in a suitable case, e.g. in mating cylindrical metal shells such as in a coin-type cell, in an elongated cylindrical AAA, AA, C or D cell casing or in a replaceable battery pack. Alternatively, the cell may be sealed in a Li-ion format such as in an 18650 format, in a pouch cell, etc. The cell may be used in a variety of devices, including portable computers, tablet displays, personal digital assistants, mobile telephones, motorized devices (e.g. personal or household appliances and vehicles), instruments, illumination devices (e.g. flashlights) and heating devices. The cell may have particular utility in low-cost mass market electrical and electronic devices such as flashlights, radios, CD players and the like, which heretofore have usually been powered by non-rechargeable batteries such as alkaline cells.

Positive Electrode:

The cell includes a positive electrode having a recharged potential. The cell may have a single positive electrode or more than one positive electrode. The terminology "positive electrode" may describe one of a pair of electrodes that, under typical circumstances, and when the cell is fully charged, will have the highest potential that it can achieve under normal operation. This terminology also typically describes the same physical electrode under all cell operating conditions even if the electrode temporarily (e.g. due to cell overdischarge) is driven to or exhibits a potential less than that of another (e.g. negative) electrode.

The positive electrode is not particularly limited and may be any known in the art. In various embodiments, the positive electrode may be or include the following (with approximate recharged potentials) $FeS_2$ (3.0 V vs. $Li/Li^+$), $LiCoPO_4$ (4.8 V vs. $Li/Li^+$), $LiFePO_4$ (3.6 V vs. $Li/Li^+$), $Li_2FeS_2$ (3.0 V vs. $Li/Li^+$), $Li_2FeSiO_4$ (2.9 V vs. $Li/Li^+$), $LiMn_2O_4$ (4.1 V vs. $Li/Li^+$), $LiMnPO_4$ (4.1 V vs. Li/Li+), $LiNiPO_4$ (5.1 V vs. Li/Li+), $LiV_3O_8$ (3.7 V vs. $Li/Li^+$), $LiV_6O_{13}$ (3.0 V vs. $Li/Li^+$), $LiVOPO_4$ (4.15 V vs. $Li/Li^+$), $LiVOPO_4F$ (4.3 V vs. $Li/Li^+$), $Li_3V_2(PO_4)_3$ (4.1 V (2 Li) or 4.6 V (3 Li) vs. $Li/Li^+$), $MnO_2$ (3.4 V vs. $Li/Li^+$), $MoS_3$ (2.5 V vs. $Li/Li^+$), sulfur (2.4 V vs. $Li/Li^+$), $TiS_2$ (2.5 V vs. $Li/Li^+$), $TiS_3$ (2.5 V vs. $Li/Li^+$), $V_2O_5$ (3.6 V vs. $Li/Li^+$), $V_6O_{13}$ (3.0 V vs. $Li/Li^+$), $LiCoO_2$ (4.2 V vs. $Li/Li^+$), $LiNiMnCoO_2$ (4.2 V vs. $Li/Li^+$), $LiNiCoAlO_2$ (4.3 V vs. $Li/Li^+$), and combinations thereof. In one embodiment, the positive electrode includes $LiFePO_4$, $Li_2FeSiO_4$, $MnO_2$, $Li_xMnO_2$, $LiNiMnCoO_2$, and/or $LiNiCoAlO_2$, wherein x is 0.3 to 0.4. Some positive electrode materials may, depending upon their structure or composition, be charged at a number of voltages, and thus may be used as a positive electrode if an appropriate form and appropriate cell operating conditions are chosen. Electrodes that are or include $LiFePO_4$, $Li_2FeSiO_4$, $Li_xMnO_2$ (wherein x is about 0.3 to about 0.4, and made for example by heating a stoichiometric mixture of electrolytic manganese dioxide and LiOH to about 300 to about 400° C.) or $MnO_2$ (made for example by heat treatment of electrolytic manganese dioxide to about 350° C.) can provide cells having especially desirable performance characteristics when used with the redox shuttle having oxidation potentials of about 3.5, 4, 4.5, or 5, V. The positive electrode may include additives, e.g. carbon black, flake graphite and the like. The positive electrode may be in any convenient form including foils, plates, rods, pastes or as a composite made by forming a coating of the positive electrode material on a conductive current collector or other suitable support. In various embodiments, the positive electrode is or includes $LiFePO_4$, $Li_2FeSiO_4$, $MnO_2$, or $Li_xMnO_2$ wherein x is 0.3 to 0.4. In other embodiments, the positive electrode is or includes $Li[B(C_2O_4)_2]$, $Li[BF_2(C_2O_4)]$, $Li[PF_2(C_2O_4)_2]$, $LiClO_4$, $LiBF_4$, $LiAsF_6$, $LiPF_6$, $Li[CF_3SO_3]$, $Li[N(CF_3SO_2)_2]$, $Li[C(CF_3SO_2)_3]$, $Li[N(SO_2C_2F_5)_2]$, lithium alkyl fluorophosphates, or combinations thereof. In various embodiments, the positive electrode is chosen from $LiFePO_4$, $LiCoO_2$, $LiMN_2O_4$, $LiNiMnCoO_2$ and $LiNiCoAlO_2$, and combinations thereof.

Referring back, the terminology "recharged potential" typically describes a value $E_{cp}$ measured relative to $Li/Li^+$ by constructing a cell including the positive electrode, a negative electrode, a charge-carrying electrolyte, and no substituted phenothiazine, substituted carbazole, substituted phenazine, or other redox shuttle, carrying out a charge/discharge cycling test and observing the potential at which the positive electrode becomes delithiated during the first charge cycle to a lithium level corresponding to at least 90% of the available recharged cell capacity. For some positive electrodes (e.g. $LiFePO_4$), this lithium level may correspond to approximately complete delithiation (e.g. to $Li_0FePO_4$). For other positive electrodes (e.g. some electrodes having a layered lithium-including structure), this lithium level may correspond to partial delithiation.

Negative Electrode:

The cell includes a negative electrode. The cell may have a single negative electrode or more than one negative electrode. The terminology "negative electrode" may describe one of a pair of electrodes that, under normal circumstances and when the cell is fully charged, have the lowest potential. This terminology also typically describes the same physical electrode under all cell operating conditions even if such electrode is temporarily (e.g. due to cell overdischarge) driven to or exhibits a potential above that of the other (e.g. positive) electrode.

The negative electrode is not particularly limited and may be any known in the art. Non-limiting examples of negative electrodes include graphitic carbons e.g. those having a spacing between (002) crystallographic planes, $d_{002}$ of 3.45 Angstroms>$d_{002}$>3.354 Angstroms and existing in forms such as powders, flakes, fibers or spheres (e.g. mesocarbon microbeads); lithium metal; $Li_{4/3}Ti_{5/3}O_4$; Sn—Co-based amorphous negative electrodes, and combinations thereof. A negative electrode including extractible lithium (e.g. a lithium metal electrode, extractible lithium alloy electrode, or electrode including powdered lithium) may be employed so that extractible lithium can be incorporated into the positive electrode during initial discharging. The negative electrode may include additives, e.g. carbon black. The negative electrode may be in any convenient form including foils, plates, rods, pastes or as a composite made by forming a coating of the negative electrode material on a conductive current collector or other suitable support. In various embodiments, the negative electrode includes graphitic carbon, lithium metal or a lithium alloy or a combination thereof.

In addition to the above, the rechargeable lithium-ion cell also includes a charge-carrying electrolyte. The charge-carrying electrolyte includes a charge-carrying medium and a lithium salt.

Charge-Carrying Electrolyte:

The charge-carrying electrolyte is not particularly limited and may be any known in the art. Typically, the charge-carrying electrolyte provides a charge-carrying pathway between the positive and negative electrodes, and initially includes at least the charge-carrying medium and the lithium salt. The charge-carrying electrolyte may include other additives typically utilized in the art. The charge-carrying electrolyte may be in any convenient form including liquids and gels.

The charge-carrying electrolyte may include the redox shuttle (as described in detail below) that may or may not be dissolved therein. For example, the charge-carrying electrolyte may be formulated without the redox shuttle and incorporated into a cell whose positive or negative electrode includes a dissolvable redox shuttle that can dissolve into the charge-carrying electrolyte after cell assembly or during the first charge-discharge cycle, so that the charge-carrying electrolyte will include a redox shuttle once the cell has been put into use.

Charge-Carrying Medium:

The charge-carrying medium is also not particularly limited and may be any known in the art. Non-limiting examples of suitable charge-carrying medium include liquids and gels capable of solubilizing sufficient quantities of lithium salt and the redox shuttle so that a suitable quantity of charge can be transported from the positive electrode to negative electrode. The charge-carrying medium can typically be used over a wide temperature range, e.g. from about −30° C. to about 70° C. without freezing or boiling, and is typically stable in the electrochemical window within which the electrodes operate. Non-limiting examples of charge carrying mediums include, but are not limited to, ethylene carbonate, propylene carbonate, dimethyl carbonate, diethyl carbonate, ethylmethyl carbonate, butylene carbonate, vinylene carbonate, fluoroethylene carbonate, fluoropropylene carbonate, γ-butyrolactone, methyl difluoroacetate, ethyl difluoroacetate, dimethoxyethane, diglyme (bis(2-methoxyethyl)ether), and combinations thereof. In various embodiments, the charge-carrying medium includes ethylene carbonate, propylene carbonate, dimethyl carbonate, diethyl carbonate, ethylmethyl carbonate, or combinations thereof.

The charge-carrying medium is typically present in an amount of from 60% to 99% by weight, from 65% to 95% by weight, or from 70% to 90% by weight, each based on a total weight of the charge-carrying electrolyte. Alternatively, all values and ranges of values within those values described above are hereby expressly contemplated in various non-limiting embodiments.

Lithium Salt:

The lithium salt is also not particularly limited and may include any known in the art. Non-limiting examples of suitable lithium salts are stable and soluble in the chosen charge-carrying medium and perform well in the chosen lithium-ion cell, and can include or be $LiPF_6$, $LiBF_4$, $LiClO_4$, lithium bis(oxalato)borate ("LiBOB"), $LiN(CF_3SO_2)_2$, $LiN(C_2F_5SO_2)_2$, $LiAsF_6$, $LiC(CF_3SO_2)_3$ and combinations thereof.

The lithium salt is typically present in an amount of from 1 to 40, from 5 to 35, or from 10 to 30, parts by weight per 100 parts by weight of the charge-carrying electrolyte. Alternatively, all values and ranges of values within those values described above are hereby expressly contemplated in various non-limiting embodiments.

Redox Shuttle:

The cell includes a redox shuttle. In various embodiments, the terminology "redox shuttle" describes an electrochemically reversible moiety or compound that can become oxidized at the positive electrode, migrate to the negative electrode, become reduced at the negative electrode to reform the unoxidized (or less-oxidized) shuttle species, and migrate back to the positive electrode. Alternatively, the redox shuttle may be described as an electroactive compound, which may be heterocyclic, wherein the terminology "electroactive" is as understood by those of skill in the art. Alternatively, any one of more of the compounds described below, e.g. substituted phenothiazines, substituted phenazines, and/or substituted carbazoles, may be described as a redox shuttle and/or a compound that protects against overcharging.

A redox shuttle may have an oxidation potential above the recharged potential of the positive electrode and may serve as a cyclable redox chemical shuttle providing cell overcharge protection. The terminology "oxidation potential" typically refers to a value $E_{1/2}$ which may be measured by dissolving the redox shuttle in the chosen charge-carrying electrolyte, measuring current vs. applied voltage using cyclic voltammetry and a platinum or glassy carbon working electrode, a counter electrode and a suitable reference electrode that has been previously referenced to $Li/Li^+$ and determining the potentials $E_{pa}$ (i.e., the potential at which the peak anodic current is observed) and $E_{pc}$ (i.e., the potential at which the peak cathodic current is observed), relative to $Li/Li^+$. $E_{1/2}$ is typically taken as the average of $E_{pa}$ and $E_{pc}$. Shuttle oxidation potentials may be estimated (to provide a value "$E_{obs}$") by constructing a cell including the shuttle, carrying out a charge/discharge cycling test, and observing during a charging sequence the potential at which a voltage plateau indicative of shuttle oxidation and reduction occurs. The observed result may be corrected by the amount of the negative electrode potential vs. $Li/Li^+$ to provide an $E_{obs}$ value relative to $Li/Li^+$. Shuttle oxidation potentials may be approximated (to provide a value "$E_{calc}$") using modeling software such as GAUSSIAN 03 from Gaussian Inc. to predict oxidation potentials (e.g. for compounds whose $E_{1/2}$ is not known) by correlating model ionization potentials to the oxidation potentials and lithium-ion cell behavior of measured compounds.

The redox shuttle may, for example, have an oxidation potential from 3.5 to 5, from 3.6 to 5, from 3.7 to 5, from 3.8 to 5, from 3.9 to 4.9, from 4 to 4.8, from 4.1 to 4.7, from 4.2 to 4.6, from 4.3 to 4.5, or from 4.4 to 4.5, V, above the recharged potential of the positive electrode. For example, $LiFePO_4$ positive electrodes have a recharged potential of about 3.6 V vs. $Li/Li^+$, and one embodiment of a redox shuttle has an oxidation potential of about (3.5-3.7) to about 4.2 V vs. $Li/Li^+$. $Li_2FeSiO_4$ positive electrodes have a recharged potential of around 2.8 V vs. Li/Li+, and another embodiment of a redox shuttle has an oxidation potential of about 3.5 V to about 4.0 V vs. $Li/Li^+$. $Li_xMnO_2$ (where x is about 0.3 to 0.4) and $MnO_2$ positive electrodes have a recharged potential of about 3.4 V vs. $Li/Li^+$, and another embodiment of a redox shuttle has an oxidation potential of about 3.7 to about 4.4 V vs. $Li/Li^+$. In one embodiment, the redox shuttle has an oxidation potential from 3.5 to 5 V as compared to $Li/Li^+$. In another embodiment, the redox shuttle has an oxidation potential from 4 to 5 V as compared to $Li/Li^+$. In still another embodiment, the redox shuttle has an oxidation potential from 3.5 to 4 V as compared to $Li/Li^+$. In a further embodiment, the redox shuttle has an oxidation potential from 3.7 to 3.9 V as compared to Li/Li+, e.g. for $LiFePO_4$ cells. Alternatively, all values and ranges of values within those values described above are hereby expressly contemplated in various non-limiting embodiments.

The redox shuttle may be disposed in a charge-carrying electrolyte and/or in another location in the cell. When an attempt is made to charge the cell above this oxidation potential, the oxidized redox shuttle carries a charge quantity corresponding to the applied charging current to the negative electrode, thus preventing or at least minimizing cell overcharge. In various embodiments, the redox shuttle is cyclable to provide at least 10, at least 30, at least 100, or at least 500 cycles of overcharge protection at a charging voltage sufficient to oxidize the redox shuttle and at an overcharge charge flow equivalent to 100% of the cell capacity during each cycle. In alternative embodiments, the aforementioned number of cycles is 500-1000, greater than 1,000, from 1,000 to 10,000, or even greater than 10,000. Alternatively, all values and ranges of values within those values described above are hereby expressly contemplated in various non-limiting embodiments. The redox shuttle is different from the positive electrode and typically has an oxidation potential different from and higher (e.g. more positive) than the recharged potential of the positive electrode. The potential of the redox shuttle may be slightly greater than the recharged potential of the positive electrode, less than the potential at which irreversible cell damage might occur, and less than the potential at which excessive cell heating or outgassing may occur.

In various embodiments, the substituted phenothiazine is utilized alone as a redox shuttle or in combination with other redox shuttles. Alternatively, other redox shuttles may be used to the complete exclusion of the substituted phenothiazine. For example, various embodiments of the cell of this disclosure are entirely free of the substituted phenothiazine and include alternative redox shuttles instead.

The redox shuttle typically has the following structure:

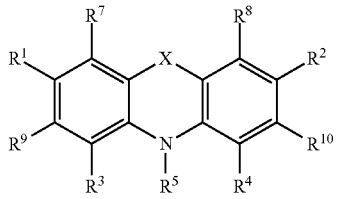

In this structure, X is a covalent bond (such that the center ring is a five membered ring), a sulfur atom (S), or a nitrogen atom bonded to $R^6$ (N—$R^6$). If X is a covalent bond, then the center ring is a five membered ring (such as in a carbazole) wherein the carbon atoms of the two benzyl rings (i.e., the carbon atoms are meta to $R^1$ and $R^2$) are singly bonded to each other. Moreover, each of $R^1$, $R^2$, $R^3$, $R^4$, $R^5$, $R^6$, $R^7$, $R^8$, $R^9$ and $R^{10}$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, [an oxo group,] an alkyl ether group, a trialkylammoniumalkyl group, a phosphate group, a phosphonate group, or an alkyl phosphonate group, and wherein one of $R^3$ and $R^4$ is optionally a hydrogen atom. Moreover, any one of $R^1$, $R^2$, $R^3$, $R^4$, $R^5$, $R^6$, $R^7$, $R^8$, $R^9$ and $R^{10}$ for any structure herein may be as described in greater detail below. Said differently, various non-limiting embodiments are hereby expressly contemplated wherein each of $R^1$, $R^2$, $R^3$, $R^4$, $R^5$, $R^6$, $R^7$, $R^8$, $R^9$ and $R^{10}$ are independently chosen as described in all sections below. In various embodiments, each of $R^1$ and $R^2$ is independently an alkyl group, a haloalkyl group (including perhaloalkyl), or an alkyl ether group and at least one of $R^3$ and $R^4$ is an alkyl group, a haloalkyl group (including perhaloalkyl), an alkyl ether group, an acyl group, or a haloacyl group. Without intending to be bound by any particular theory, it is believed that substitution at these positions surprisingly increases the oxidation potential through a steric effect. In other embodiments, each of $R^1$, $R^2$, $R^3$, $R^4$, and $R^5$ are chosen from alkyl groups, alkyl ether groups, acetyl groups, and $CF_3$ groups. Alternative redox shuttles include substituted carbazoles, substituted phenazines, and combinations thereof.

Substituted Phenothiazine:

The substituted phenothiazine typically has the following structure:

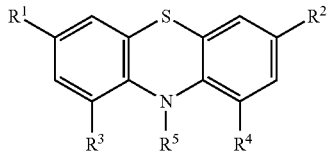

In various embodiments, each of $R^1$, $R^2$, $R^3$, $R^4$, and $R^5$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, [an oxo group,] an alkyl ether group, a trialkylammoniumalkyl group, a phosphate group, a phosphonate group, or an alkyl phosphonate group. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom.

In other embodiments, each of $R^1$ and $R^2$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, [an oxo group,] an alkyl ether group, a trialkylammoniumalkyl group, a phosphate group, a phosphonate group, or an alkyl phosphonate group. In related embodiments, each of $R^3$ and $R^4$ is independently an alkyl group having 1-6 or 1-12 carbon atoms or a haloalkyl group (e.g. mono-, di-, or tri-halo) having 1 to 12 carbon atoms. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom. In other embodiments, $R^5$ is an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an alkyl ether group having 1-6 or 1-12 carbon atoms, or a trialkylammoniumalkyl group having 1-6 or 1-12 carbon atoms. Alternatively, all values and ranges of values within those values described above are hereby expressly contemplated in various non-limiting embodiments.

In further embodiments, each of $R^1$ and $R^2$ is independently an alkyl group having 1, 2, 3, 4, 5, or 6 carbon atoms or 1-12 carbon atoms, a trifluoromethyl group, a halo group, a cyano group, an alkyl ether group having 1 to 12 carbon atoms, an alkyl ether group having 1-12 carbon atoms, or a trialkylammoniumalkyl group having 1 to 12 carbon atoms. In other embodiments, each of $R^3$ and $R^4$ are independently an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an acyl group, a haloacyl group, or a perhaloacyl group. Non-limiting examples of suitable alkyl groups are methyl, ethyl, propyl, iso-propyl, butyl, iso-butyl, sec-butyl, tert-butyl, neopentyl, n-pentyl, hexyl, octyl, and the like, as appreciated by those of skill in the art. Alternatively, all values and ranges of values within those values described above are hereby expressly contemplated in various non-limiting embodiments.

In still other embodiments, each of $R^3$ and $R^4$ are sterically bulky. The terminology "sterically bulky" is appreciated by those of skill in the art. For example, each of $R^3$ and $R^4$ may be a $C_2$-$C_4$ alkyl group, such as an iso-propyl, butyl, iso-butyl, sec-butyl, tert-butyl group. These types of groups may shift a potential to a more positive value without sacrificing (or at least minimizing an effect on) stability of the compound. Alternatively, each of $R^3$ and $R^4$ may be a $C_2$-$C_5$ alkyl group and may include those groups described above and neopentyl groups. In still other embodiments, each of $R^3$ and $R^4$ may be methyl and/or $CF_3$ groups. In some embodiments, relative to phenothiazines, phenazines, and carbazoles, calculations show that a methyl groups, haloalkyl groups (e.g. mono-, di-, or tri-halo), and perhaloalkyl groups are sufficiently sterically bulky to induce a positive shift of the oxidation potential.

In various embodiments, each of $R^1$ and $R^2$ is independently an alkyl group, a haloalkyl group (including perhaloalkyl), or an alkyl ether group and at least one of $R^3$ and $R^4$ is an alkyl group, a haloalkyl group (including perhaloalkyl), an alkyl ether group, an acyl group, or a haloacyl group. In other embodiments, each of $R^1$, $R^2$, $R^3$, $R^4$, and $R^5$ are chosen from alkyl groups, alkyl ether groups, acetyl groups, and $CF_3$ groups. Without intending to be bound by any particular theory, it is believed that substitution at these positions surprisingly increases the oxidation potential through a steric effect.

The redox shuttle, e.g. the substituted phenothiazine, may be included in the cell in any amount as determined by one of skill in the art. In various embodiments, the substituted phenothiazine is present in an amount of from 0.05 to 10, from 1 to 10, from 2 to 9, from 3 to 8, from 4 to 7, or from 5 to 6, parts by weight per 100 parts by weight of the charge-carrying electrolyte. Alternatively, all values and ranges of values within those values described above are hereby expressly contemplated in various non-limiting embodiments. Amounts of the substituted phenothiazine, substituted carbazole, substituted phenazine (and/or any of the redox shuttles described herein) may be chosen based on solubility, diffusion coefficients, the need for overcharge protection, etc.

Substituted Phenazine:

The substituted phenazine typically has one of the following structures:

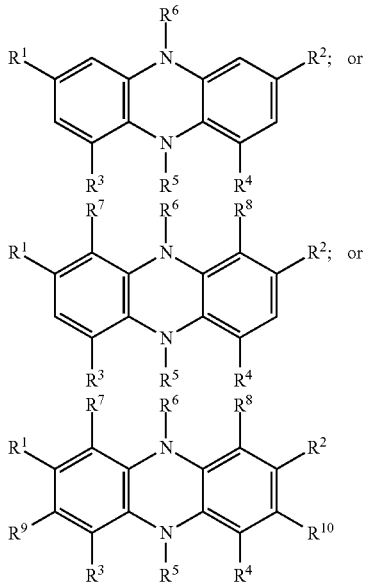

Without intending to be bound by any particular theory, it is believed that phenazines have the lowest baseline oxidation potential, phenothiazines have a mid-level oxidation potential, and carbazoles have the highest baseline oxidation potential. In various embodiments, steric effects of ortho substitution at the 1,8 positions of the carbazole may be relatively modest. In addition, steric effects of ortho substitution at the 1, 4, 6, 9 positions of phenazine may be larger.

In these structures, each of $R^1$, $R^2$, $R^3$, $R^4$, $R^5$, $R^6$, $R^7$, and $R^8$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, [an oxo group,] an alkyl ether group, a trialkylammoniumalkyl group, a phosphate group, a phosphonate group, or an alkyl phosphonate group. In one embodiment, one of $R^3$ and $R^4$ and/or one of $R^7$ and $R^8$ is a hydrogen atom whereas the other of $R^3$ and $R^4$ and/or $R^7$ and $R^8$ is not a hydrogen atom. Each of $R^9$ and $R^{10}$ may independently be the same or different from any one of $R^1$, $R^2$, $R^3$, $R^4$, $R^5$, $R^6$, $R^7$, and/or $R^8$ described above. In other embodiments, any or all of $R^1$, $R^2$, $R^9$, and $R^{10}$ can be H. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom.

In other embodiments, each of $R^1$ and $R^2$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, [an oxo group,] an alkyl ether group, a trialkylammoniumalkyl group, a phosphate group, a phosphonate group, or an alkyl phosphonate group. In related embodiments, each of $R^3$ and $R^4$ is independently an alkyl group having 1 to 12 carbon atoms or a haloalkyl group (e.g. mono-, di-, or tri-halo) having 1 to 12 carbon atoms. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom. In other embodiments, each of $R^5$ and $R^6$ is independently an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an alkyl ether group having 1-12 carbon atoms, or a trialkylammoniumalkyl group. In still other embodiments, each of $R^7$ and $R^8$ are the same or different than $R^3$ and $R^4$, respectively. Alternatively, each of $R^7$ and $R^8$ can be any group described above relative to $R^3$ and/or $R^4$. Alternatively, all values and ranges of values within those values described above are hereby expressly contemplated in various non-limiting embodiments.

In further embodiments, each of $R^1$ and $R^2$ is independently an alkyl group having 1, 2, 3, 4, 5, or 6 carbon atoms or 1-12 carbon atoms, a trifluoromethyl group, a halo group, a cyano group, an alkyl ether group having 1 to 12 carbon atoms, or a trialkylammoniumalkyl group having 1 to 12 carbon atoms. In other embodiments, each of $R^3$ and $R^4$ are independently an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an acyl group, or a haloacyl group. Alternatively, all values and ranges of values within those values described above are hereby expressly contemplated in various non-limiting embodiments.

In still other embodiments, each of $R^3$ and $R^4$ are sterically bulky. The terminology "sterically bulky" is appreciated by those of skill in the art. For example, each of $R^3$ and $R^4$ may be a $C_2$-$C_4$ alkyl group, such as an iso-propyl, butyl, iso-butyl, sec-butyl, tert-butyl group. These types of groups may shift a potential to a more positive value without sacrificing (or at least minimizing an effect on) stability of the compound. Alternatively, each of $R^3$ and $R^4$ may be a $C_2$-$C_5$ alkyl group and may include those groups described above and neopentyl groups. In still other embodiments, each of $R^3$ and $R^4$ may be methyl and/or $CF_3$ groups. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom. In some embodiments, relative to phenothiazines, phenazines, and carbazoles, calculations show that a methyl groups, haloalkyl groups (e.g. mono-, di-, or tri-halo) and perhaloalkyl groups are sufficiently sterically bulky to induce a positive shift of the oxidation potential.

In various embodiments, each of $R^1$ and $R^2$ is independently an alkyl group, a haloalkyl group (including perhaloalkyl), or an alkyl ether group and at least one of $R^3$ and $R^4$ is an alkyl group, a haloalkyl group (including perhaloalkyl), an alkyl ether group, an acyl group, or a haloacyl group. In other embodiments, each of R', $R^2$, $R^3$, $R^4$, and $R^5$ are chosen from alkyl groups, alkyl ether groups, acetyl groups, and $CF_3$ groups. Without intending to be bound by any particular theory, it is believed that substitution at these positions surprisingly increases the oxidation potential through a steric effect.

The redox shuttle, e.g. the substituted phenazine, may be included in the cell in any amount as determined by one of skill in the art. In various embodiments, the substituted phenazine is present in an amount of from 0.05 to 10, from 1 to 10, from 2 to 9, from 3 to 8, from 4 to 7, or from 5 to 6, parts by weight per 100 parts by weight of the charge-carrying electrolyte. Alternatively, all values and ranges of values within those values described above are hereby expressly contemplated in various non-limiting embodiments.

Substituted Carbazole:

In other embodiments, the substituted carbazole typically has the following structure:

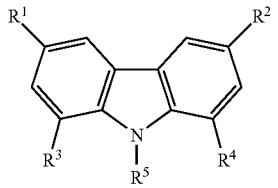

In these embodiments, X is the covalent bond such that the center ring is a five membered ring, as shown immediately above. In various embodiments, each of $R^1$, $R^2$, $R^3$, $R^4$, and $R^5$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, [an oxo group,] an alkyl ether group, a trialkylammoniumalkyl group, a phosphate group, a phosphonate group, or an alkyl phosphonate group. In one embodiment, one of $R^3$ and $R^4$ is a hydrogen atom and the other of $R^3$ and $R^4$ is not a hydrogen atom.

In other embodiments, each of $R^1$ and $R^2$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, [an oxo group,] an alkyl ether group, a trialkylammoniumalkyl group, a phosphate group, a phosphonate group, or an alkyl phosphonate group. In related embodiments, each of $R^3$ and $R^4$ is independently an alkyl group having 1 to 12 carbon atoms or a haloalkyl group (e.g. mono-, di-, or tri-halo) having 1 to 12 carbon atoms. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom. In other embodiments, $R^5$ is an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an alkyl ether group having 1-6 or 1-12 carbon atoms, or a trialkylammoniumalkyl group having 1-6 or 1-12 carbon atoms. Alternatively, all values and ranges of values within those values described above are hereby expressly contemplated in various non-limiting embodiments.

In further embodiments, each of $R^1$ and $R^2$ is independently an alkyl group having 1, 2, 3, 4, 5, or 6 carbon atoms or 1-12 carbon atoms, a trifluoromethyl group, a halo group, a cyano group, an alkyl ether group having 1-6 or 1-12 carbon atoms, or a trialkylammoniumalkyl group having 1-12 carbon atoms. In other embodiments, each of $R^3$ and $R^4$ are independently an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an acyl group, or a haloacyl group. Alternatively, all values and ranges of values within those values described above are hereby expressly contemplated in various non-limiting embodiments.

In still other embodiments, each of $R^3$ and $R^4$ are sterically bulky. The terminology "sterically bulky" is appreciated by those of skill in the art. For example, each of $R^3$ and $R^4$ may be a $C_2$-$C_4$ alkyl group, such as an iso-propyl, butyl, iso-butyl, sec-butyl, tert-butyl group. These types of groups may shift a potential to a more positive value without sacrificing (or at least minimizing an effect on) stability of the compound. However, and without intending to be bound by any particular theory, it is believed that the effect of bulky substituents is typically larger for phenothiazine than for carbazole. Alternatively, each of $R^3$ and $R^4$ may be a $C_2$-$C_5$ alkyl group and may include those groups described above and neopentyl groups. The identity of the groups attached to the nitrogen of the carbazole may be chosen to increase or decrease solubility, by one of skill in the art. In still other embodiments, each of $R^3$ and $R^4$ may be methyl and/or $CF_3$ groups. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom. In some embodiments, relative to phenothiazines, phenazines, and carbazoles, calculations show that a methyl groups, haloalkyl groups (e.g. mono-, di-, or tri-halo), and perhaloalkyl groups are sufficiently sterically bulky to induce a positive shift of the oxidation potential.

In various embodiments, each of $R^1$ and $R^2$ is independently an alkyl group, a haloalkyl group (including perhaloalkyl), or an alkyl ether group and at least one of $R^3$ and $R^4$ is an alkyl group, a haloalkyl group (including perhaloalkyl), an alkyl ether group, an acyl group, or a haloacyl group. In other embodiments, each of $R^1$, $R^2$, $R^3$, $R^4$, and $R^5$ are chosen from alkyl groups, alkyl ether groups, acetyl groups, and $CF_3$ groups. Without intending to be bound by any particular theory, it is believed that substitution at these positions surprisingly increases the oxidation potential through a steric effect.

The redox shuttle, e.g. the substituted carbazole, may be included in the cell in any amount as determined by one of skill in the art. In various embodiments, the substituted carbazole is present in an amount of from 0.05 to 10, from 1 to 10, from 2 to 9, from 3 to 8, from 4 to 7, or from 5 to 6, parts by weight per 100 parts by weight of the charge-carrying electrolyte. Alternatively, all values and ranges of values within those values described above are hereby expressly contemplated in various non-limiting embodiments.

Mixtures of two or more redox shuttles (or substituted phenothiazines, substituted carbazole, substituted phenazine, or other redox shuttle) having different electrochemical potentials vs. $Li/Li^+$ may also be employed. For example, a first redox shuttle operative at 3.7 V and a second redox shuttle operative at 3.9 V may both be employed in a single cell. If after many charge/discharge cycles the first redox shuttle degrades and loses effectiveness, the second redox shuttle (which would typically not meanwhile have been oxidized while the first redox shuttle was operative) can take over and provide a further (albeit higher $E_{1/2}$) margin of safety against overcharge damage. The redox shuttle can also provide overdischarge protection to a cell or to a battery of series-connected cells. Redox shuttles can also be used for cell balancing purposes as well as or even in lieu of overcharge protection. For example, redox shuttles could be used to reduce the cost of cell-balancing associated electronics.

The redox shuttle can be dissolved or dissolvable in the charge-carrying electrolyte in an amount sufficient to provide overcharge protection at the intended charging rate. The maximum shuttle current for a singly ionized shuttle is typically given by the following equation, where F is Faraday's number, A is the electrode area, D is an effective diffusion constant of the redox shuttle species (taking into account both oxidized and reduced forms of the redox shuttle), C is the total concentration of the redox shuttle species and d is the distance between the positive and negative electrodes:

$$I_{max}=FADC/d$$

To obtain a large redox shuttle current, the charge-carrying electrolyte can promote a large diffusion constant D to the redox shuttle and/or support a high redox shuttle concentration C. Thus the charge-carrying electrolyte can initially or eventually include a dissolved quantity of the substituted phenothiazine, substituted carbazole, substituted phenazine, and/or the redox shuttle. The redox shuttle diffusion constant D typically increases as the viscosity of the charge-carrying electrolyte decreases. Non-limiting concentrations of the substituted phenothiazine, substituted carbazole, substituted phenazine, and/or the redox shuttle in the charge-carrying electrolyte are about 0.05 M up to a limit of solubility, more than 0.1 M up to a limit of solubility, about 0.2 M up to a limit of solubility or about 0.3 M up to a limit of solubility. The concentration of the substituted phenothiazine, substituted carbazole, substituted phenazine, and/or the redox shuttle may be increased by incorporating a suitable cosolvent in the charge-carrying electrolyte. Non-limiting co-solvents include acetonitrile, benzene, ethers (e.g. dimethyl ether), esters (e.g. ethyl acetate or methyl acetate), lactones (e.g. gamma-butyrolactone), pyridine, tetrahydrofuran, toluene and combinations thereof. In other embodiments, the co-solvent is chosen from ethylene carbonate, propylene carbonate, dimethyl carbonate, diethyl carbonate, ethylmethyl carbonate, butylene carbonate, vinylene carbonate, fluoroethylene carbonate, fluoropropylene carbonate, γ-butyrolactone, methyl difluoroacetate, ethyl difluoroacetate, dimethoxyethane, diglyme (bis(2-methoxyethyl)ether), and combinations thereof. In still other embodiments, the co-solvent is chosen from ethylene carbonate, propylene carbonate, dimethyl carbonate, diethyl carbonate, ethylmethyl carbonate, or combinations thereof.

The redox shuttle may alternatively be described as including one or more sterically bulky groups at sites adjacent to the nitrogen atom(s). Typically, the inclusion of electron-donating groups would be expected to shift the oxidation potential of the redox shuttle to a less positive number. However, in the instant disclosure, it is surprisingly discovered that sterically bulky groups, even if they are electron-donating groups, do precisely the opposite and shift the oxidation potential of the redox shuttle to a more positive number.

In various embodiments, the redox-shuttle may be 1-$CF_3$-3,6-bis(t-Bu)carbazole; 1-acetyl-3,6-bis(t-Bu)carbazole; 1-acetyl-8-$CF_3$-3,6-bis(t-Bu)carbazole; 1,8-bis($CF_3$)-3,6-bis(t-Bu)carbazole; the phenothiazines analogous to the aforementioned compounds; 1,4,6,9-tetra(t-Bu)phenazine; 1,6-bis(t-Bu)-4,9-bis($CF_3$)phenazine; 1,6-bis(t-Bu)-3,8-bis($CF_3$)phenazine; and/or any analogs having substitution at N such as $C_1$-$C_{20}$ alkyl, alkyl ether or oligoether, trialkylammonium alkyl, or other solubilizing groups. In other embodiments, the solubilizing group may be any known in the art.

For example, the solubilizing groups may be as described in U.S. Pat. No. 6,445,486, which is expressly incorporated herein by reference in various non-limiting embodiments. Moreover, it is also contemplated that any compounds described in the Examples below may be utilized in any embodiments described herein in various non-limiting embodiments.

Referring back to the cell itself, the cell may also include a porous cell separator disposed between the positive and negative electrodes and through which charge-carrying species (including the oxidized or reduced substituted phenothiazine, substituted carbazole, or substituted phenazine, and/or redox shuttle) may pass.

In various embodiments, the redox shuttle provides overcharge protection to the cell after at least 30, 40, 50, 60, 70, 80, 90, 100, 200, 300, 400, 500, 600, 700, 800, 900, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, or even greater, charge-discharge cycles at a charging voltage sufficient to oxidize the redox shuttle and at an overcharge charge flow equivalent to 100% of the cell capacity during each charge-discharge cycle. Alternatively, all values and ranges of values within those values described above are hereby expressly contemplated in various non-limiting embodiments.

This disclosure also provides an article including the cell and an array of cells. The article may be any known in the art that utilizes cells (or batteries), e.g. hand-held devices, flashlights, power tools, or any of those described above. The array of cells may also be any known in the art.

Examples

Various substituted phenothiazines, substituted carbazoles, substituted phenazines, and redox-shuttles are synthesized and evaluated to determine oxidation potential. Additional theoretical calculations of oxidation potential are also performed on compounds not actually synthesized. The calculation of oxidation potential is based on the work of R. L. Wang et al., as set forth in Wang, R. L.; Buhrmester, C.; Dahn, J. R. J. Electrochem. Soc. 2006, 153, A445-A449, which is expressly incorporated by reference herein in various non-limiting embodiments.

The oxidation potential $E^0$ of a redox shuttle candidate relative to a lithium-ion cell can be determined by comparing the difference in standard free energies between the B3LYP energy $G^0$ (in electronvolts) between the shuttle S and its radical cation $S^+$:

$$E^0(S) = -\frac{[G^0(S) - G^0(S^+)]}{e} - 1.46\ \text{V}$$

All electrochemical measurements were performed in propylene carbonate including 0.2M tetraethylammonium tetrafluoroborate as a supporting electrolyte. Oxidation potentials were determined by averaging the anodic and cathodic peak potentials obtained via cyclic voltammetry (100 mV/s) or from differential pulse voltammetry. Ferrocene was used as an internal standard having $E_{0X}$=3.25 V vs. $Li/Li^+$.

The calculations, both theoretical and actual, of various substituted phenothiazines, carbazoles, and phenazines, are set forth in the tables below.

Substituted Phenothiazine Calculations:

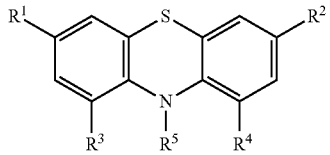

| $R^1 = R^2$ | $R^3 = R^4$ | $R^5$ | E calc ($Li/Li^+$) | E exp ($Li/Li^+$) |
|---|---|---|---|---|
| H | H | H | 3.25 | 3.49 (Commercially Available) |
| H | H | $CH_3$ | 3.36 | 3.60 (Commercially Available) |
| $CH_3$ | H | $CH_3$ | 3.22 | 3.55 |
| H | $CH_3$ | $CH_3$ | 3.49 | — |
| H | t-Bu | $CH_3$ | 3.87 | — |
| $CH_3$ | $CH_3$ | $CH_3$ | 3.38 | — |
| t-Bu | t-Bu | $CH_3$ | 3.79 | — |
| CN | H | $CH_3$ | 3.84 | 4.01 |
| CN | $CH_3$ | $CH_3$ | 3.96 | — |
| CN | t-Bu | $CH_3$ | 4.29 | — |
| $CF_3$ | $CH_3$ | $CH_3$ | 3.89 | — |
| $CF_3$ | t-Bu | $CH_3$ | 4.15 | — |
| $CH_3$ | $CF_3$ | $CH_3$ | 3.80 | — |
| H | H | $CH(CH_3)_2$ | 3.37 | — |
| H | $CH_3$ | $CH(CH_3)_2$ | 3.68 | — |
| H | H | $(CH_2)_3N(CH_2CH_3)_3$ | 3.56 | — |
| $CH_3$ | $CH_3$ | $(CH_2)_3N(CH_2CH_3)_3$ | 3.67 | — |
| $CH_3$ | t-Bu | $(CH_2)_3N(CH_2CH_3)_3$ | 3.75 | — |
| $CF_3$ | t-Bu | $(CH_2)_3N(CH_2CH_3)_3$ | 4.46 | — |
| CN | t-Bu | $(CH_2)_3N(CH_2CH_3)_3$ | 4.31 | — |
| H | H | $(CH_2)_2N(CH_3CH_2)_3$ | 3.64 | — |
| $CH_3$ | $CH_3$ | $(CH_2)_2N(CH_3CH_2)_3$ | 3.71 | — |
| $CH_3$ | t-Bu | $(CH_2)_2N(CH_3CH_2)_3$ | 4.06 | — |
| $CF_3$ | t-Bu | $(CH_2)_2N(CH_3CH_2)_3$ | 4.30 | — |
| CN | t-Bu | $(CH_2)_2N(CH_3CH_2)_3$ | 4.40 | — |
| t-Bu | $CF_3$ | $CH_3$ | 3.75 | — |

| $R^1 = R^2$ | $R^3$ | $R^4$ | $R^5$ | E calc ($Li/Li^+$) | E exp ($Li/Li^+$) |
|---|---|---|---|---|---|
| t-Bu | $CF_3$ | H | $CH_3$ | 3.49 | — |
| t-Bu | $C_2H_3O$ | H | $CH_3$ | 3.42 | — |

Preparation of 3,7-dibromo-10-methylphenothiazine (A)

1.0 g (4.69 mmol) of 10-methylphenothiazine was dissolved in 50 mL dichloromethane and placed in a round bottom flask which was covered in foil to prevent light exposure. 3.0 g of silica gel and 1.75 g of N-bromosuccinimide (9.85 mmol) were added, and the reaction was allowed to stir overnight. The mixture was filtered to remove silica and washed with 100 mL of deionized water. The organic layer was isolated, dried over $MgSO_4$, filtered to remove the drying agent, and concentrated using rotary evaporation. The white crystal product was then recrystallized from ethanol.

Preparation of 3,7,10-trimethylphenothiazine (B)

1.0 g (2.7 mmol) of (A) was dissolved in 20 mL of anhydrous tetrahydrofuran (THF) under a dry $N_2$ atmosphere in a round bottom flask, and the reaction mixture was cooled using an ice/acetone bath. 2.2 mL (5.5 mmol) of n-butyl lithium (2.5 M solution in hexanes) was added via syringe, and the reaction was allowed to stir for 1 hour. 0.48 mL of methyl iodide (11 mmol) was added via syringe, and the solution was stirred in the cold bath for 2 hours, then removed and stirred at room temperature overnight. deionized water (100 mL) was added to the reaction and the product was extracted with diethyl ether (100 mL). The organic layer was dried over $MgSO_4$, filtered to remove the drying agent, and concentrated using rotary evaporation. The product was purified by column chromatography on silica using a dichloromethane/hexanes gradient.

Preparation of 3,7-dicyano-10-methylphenothiazine (C)

1.0 g (2.7 mmol) of (A) was dissolved in 20 mL of anhydrous dimethylformamide (DMF) in a round bottom under dry $N_2$ pressure, along with 1.0 g (11.2 mmol) of copper cyanide. The solution was heated to 150° C. and stirred overnight. Ethyl acetate (100 mL) and deionized water (100 mL) were added to the cooled solution. The organic layer was dried over $MgSO_4$, filtered to remove the drying agent, and concentrated using rotary evaporation. The product was purified by column chromatography on silica using acetonitrile as eluent.

Carbazole Calculations:

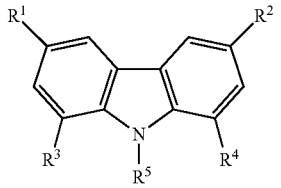

| $R^1 = R^2$ | $R^3 = R^4$ | $R^5$ | E calc ($Li/Li^+$) | E exp ($Li/Li^+$) |
|---|---|---|---|---|
| H | H | $CH_3$ | 3.86 | — |
| H | H | Et | 3.86 | 4.09(irr) (Commercially Available) |
| H | $CH_3$ | $CH_3$ | 3.69 | — |
| H | t-Bu | $CH_3$ | 3.89 | — |
| H | t-Bu | t-Bu | 3.94 | — |
| t-Bu | t-Bu | $CH_3$ | 3.71 | 4.02 |
| $CH_3$ | $CH_3$ | $CH_3$ | 3.50 | 3.80 |
| Br | $CH_3$ | $CH_3$ | 3.86 | — |
| $CF_3$ | $CH_3$ | $CH_3$ | 4.13 | — |
| CN | $CH_3$ | $CH_3$ | 4.28 | — |
| Br | t-Bu | $CH_3$ | 4.04 | — |
| $CF_3$ | t-Bu | $CH_3$ | 4.30 | — |
| CN | t-Bu | $CH_3$ | 4.43 | — |
| t-Bu | $CF_3$ | $CH_3$ | 4.13 | 4.53* |

| $R^1 = R^2$ | $R^3$ | $R^4$ | $R^5$ | E calc ($Li/Li^+$) | E exp ($Li/Li^+$) |
|---|---|---|---|---|---|
| t-Bu | $CF_3$ | H | $CH_3$ | 3.91 | 4.19* |
| t-Bu | $C_2H_3O$ | H | $CH_3$ | 3.81 | 4.12* |
| t-Bu | $C_2H_3O$ | $CF_3$ | $CH_3$ | 4.06 | |

*The experimental data (E exp) was obtained using diethyleneglycol monomethylether at $R^5$ while the calculated data (E calc) was obtained using N-methyl groups at $R^5$. The diethyleneglycolmonomethylether is used for greater solubility in electrolytes. However, and without intending to be bound by any particular theory, it is believed that there is little or no difference in the redox potential between the compounds having the diethyleneglycolmonomethylether and those having the N-methyl groups.

Preparation of 1,3,6,8-tetra(t-butyl)carbazole (I)

16.7 g (10.0 mmol) of carbazole was suspended in 70 mL of t-butylchloride and stirred at room temperature for 20 minutes. 13.5 g of $AlCl_3$ was added, which resulted in the formation of a viscous reddish purple sludge. 80 mL of t-butylchloride was added to facilitate stirring, and the mixture was allowed to stir under a $N_2$ atmosphere for 7 days. The reaction mixture was quenched with 150 mL of DI water and the crude product was extracted with 150 mL of diethyl ether, dried over $MgSO_4$, filtered to remove the drying agent, and concentrated using rotary evaporation. The crude product was purified by column chromatography on silica using a dichloromethane/hexanes gradient.

Preparation of 1,3,6,8-tetra(t-butyl)-9-methylcarbazole (II)

1.06 g (2.71 mmol) of I was dissolved in 50 mL of dry tetrahydrofuran (THF). 0.56 g (16.24 mmol) of NaH was added, and the mixture was allowed to stir for 20 minutes at room temperature under a dry $N_2$ atmosphere. 1.03 mL (10.8 mmol) of $(CH_3)_2SO_4$ was added via syringe, and the mixture was allowed to stir at room temperature for 1 week. Additional portions of both NaH (0.56 g) and $(CH_3)_2SO_4$ (1.03 mL) were introduced at the 24 hour and 72 hour marks in order to drive the reaction to completion. The crude product was obtained by quenching the reaction with DI water, extracting with dichloromethane, drying over $MgSO_4$, filtering to remove the drying agent, and concentrating using rotary evaporation. The product was purified by column chromatography on silica using a dichloromethane/hexanes gradient.

Preparation of 1,3,6,8-tetramethylcarbazole (III)

1.36 mL (10.0 mmol) of 1-bromo-2,4-dimethylbenzene, 2.405 g (12.0 mmol) of 2-bromo-4,6-dimethylaniline, 0.115 g (0.05 mmol) of palladium diacetate, 1.61 mL (1.0 mmol) of tricyclohexylphosphine (1.0 mmol), 6.365 g (3.0 mmol) of $K_3PO_4$, and 0.5 g (0.30 mmol) of KI were added to a 200 mL 3-necked round bottom flask including 125 mL of N-methyl-2-pyrrolidone (NMP) as solvent. The flask was equipped with a condenser and stir bar, and the reaction was heated to 130° C. for 72 hours. Diethyl ether (200 mL) and DI water (200 mL) were added to the reaction after cooling to room temperature. The organic layer was washed with brine (100 mL), dried over $MgSO_4$, filtered to remove the drying agent and any reduced palladium, and concentrated using rotary evaporation. The product was purified by column chromatography on silica using a dichloromethane/hexanes gradient.

Preparation of 1,3,6,8,9-pentamethylcarbazole (IV)

0.239 g (1.07 mmol) of III was dissolved in 50 mL of dry THF. 0.221 g (6.42 mmol) of NaH was added, and the mixture was allowed to stir for 20 minutes. 0.406 mL (4.28 mmol) of $(CH_3)_2SO_4$ was then added via syringe, and the reaction was allowed to stir at room temperature under a dry $N_2$ atmosphere for 72 hours. The crude product was obtained by quenching the reaction with DI water, extracting with dichloromethane, drying over $MgSO_4$, filtering to remove the drying agent, and concentrating using rotary evaporation. The product was purified by column chromatography on silica using a dichloromethane/hexanes gradient.

Preparation of 3,6-di-t-butylcarbazole (V)

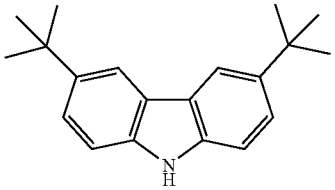

5.02 g (30.0 mmol) of carbazole was dissolved in 50 mL of dichloromethane. 4.00 g (30.0 mmol) of $AlCl_3$ was added, and the mixture was cooled to 0° C. 5.55 g (60.0 mmol) of t-butylchloride in 20 mL dichloromethane was added slowly. After addition, the ice bath was removed and the reaction was stirred at room temperature under $N_2$ for 24 hours. The reaction mixture was quenched with 150 mL of deionized water and the crude product was extracted with 150 mL of dichloromethane, dried over $MgSO_4$, filtered to remove the drying agent, and concentrated using rotary evaporation. The crude product was purified by column chromatography on silica using a dichloromethane/hexanes gradient.

Preparation of Bis(ethylene glycol) monomethylether monotosylate (VI)

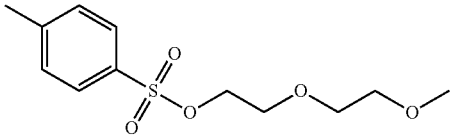

A 3-neck round bottom flask was charged with 4.70 mL (40 mmol) diethylene glycol methyl ether & 40 mL pyridine. The solution was chilled in an ice bath, under $N_2$. To this mixture, tosyl chloride dissolved in dichloromethane was added dropwise. Once the addition was complete, the reaction temperature was allowed to rise to room temperature and stirred under $N_2$ for 3 hours. The crude product was added to 100 mL of deionized water, extracted with 100 mL of dichloromethane, dried over $MgSO_4$, filtered to remove the drying agent, and concentrated using rotary evaporation. The crude product was purified by column chromatography on silica using a dichloromethane/hexanes gradient.

Preparation of 3,6-di-t-butyl-9-diethyleneglycolmonomethylether-carbazole (VII)

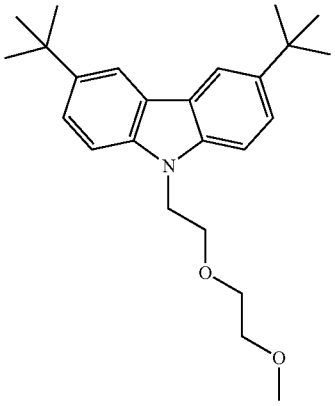

0.500 g (1.79 mmol) of V dissolved in a minimal amount of DMF was slowly dropped into a solution of 0.09 g (3.57 mmol) of NaH in 20 mL DMF. 0.978 g (3.57 mmol) of VI was then added dropwise. The mixture was heated to 65° C. and stirred for 24 hours under $N_2$. The reaction was cooled to room temperature, filtered through filter paper, poured into 100 mL of deionized water, extracted with 100 mL ethyl acetate, dried over $MgSO_4$, filtered to remove the drying agent, and concentrated using rotary evaporation. The crude product was purified by column chromatography on silica using a dichloromethane/hexanes gradient.

Preparation of 1-acetyl-3,6-di-t-butyl-9-(diethyleneglycolmonomethylether)carbazole (VIII)

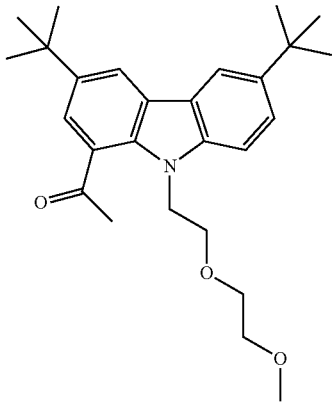

4.29 (11.25 mmol) of VII was dissolved in 50 mL of dichloromethane. 1.50 g (11.25 mmol) of $AlCl_3$ was added, and the mixture was cooled to 0° C. 1.77 g (62.50 mmol) of acetylchloride in 20 mL of dichloromethane was added slowly. After addition, the ice bath was removed and the reaction was stirred at room temperature under $N_2$ for 24 hours. Additional equivalents of $AlCl_3$ and acetylchloride were added after 24 h to push reaction to completion. The mixture was stirred overnight, quenched with 150 mL of deionized water, and the crude product was extracted with 150 mL of dichloromethane, dried over $MgSO_4$, filtered to remove the drying agent, and concentrated using rotary evaporation. The crude product was purified by column chromatography on silica using a dichloromethane/hexanes gradient.

Preparation of 3,6-di-t-butyl-1,8-diiodo-9-(diethyleneglycolmonomethylether)-carbazole (IX)

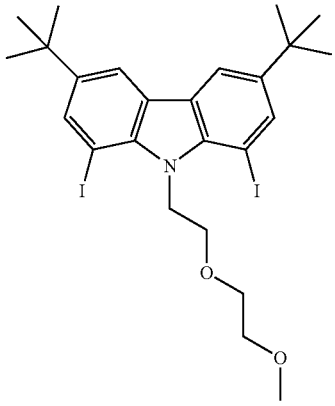

1.00 g (3.26 mmol) of VII was dissolved in 10 mL dichloromethane and 10 mL acetic acid in a round bottom flask. The flask was covered with aluminum foil to shield its contents from light, then 1.51 g (6.72 mmol) of N-iodosuccinimide was added and the flask was fitted with a rubber stopper. After 24 hours, the crude product was added to 150 mL of deionized water, extracted with 150 mL of dichloromethane, dried over $MgSO_4$, filtered to remove the drying agent, and concentrated using rotary evaporation. The crude product was purified by column chromatography on silica using a dichloromethane/hexanes gradient.

Preparation of 3,6-di-t-butyl-1,8-ditrifluoromethyl-9-(diethyleneglycol monomethylether)carbazole (X)

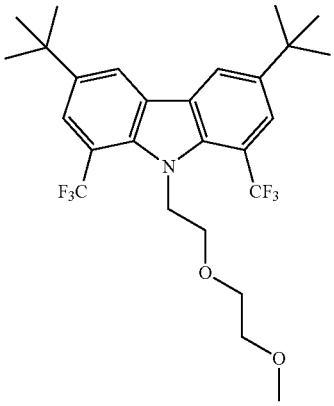

In a dry nitrogen glove box, a round bottom flask was charged with 0.1254 g (1.267 mmol) of CuCl, 0.1439 g (1.282 mmol) of KOt-Bu, 0.2063 g (1.1448 mmol) of 1,10-phenanthroline and 2.5 mL of anhydrous deaerated DMF. The reaction mixture was stirred at room temperature for 30 minutes in the glovebox. 185 μL (1.252 mmol) of $TMSCF_3$ (trifluoromethyltrimethylsilane) was added by micro-syringe to the flask and stirred at room temperature for an additional 60 minutes. Stirring was stopped, and 0.1703 g (0.2690 mmol) of (5) was added, then the flask was capped with a septum and removed from the glove box. The mixture was stirred in an oil bath for 44 hours at 50° C. The reaction mixture was cooled to room temperature. Diluted with 10 mL of diethyl ether, filtered through a pad of Celite (three times). The filtrate was washed in a separatory funnel w/sat. aq. $NaHCO_3$, draining the aqueous layer after each wash. The solution was then dried with $Na_2SO_4$, gravity filtered to remove the $Na_2SO_4$, and concentrated using rotary evaporation.

Preparation of 3,6-di-t-butyl-1,8-dibromo-9-(diethyleneglycol monomethylether)carbazole (XI)

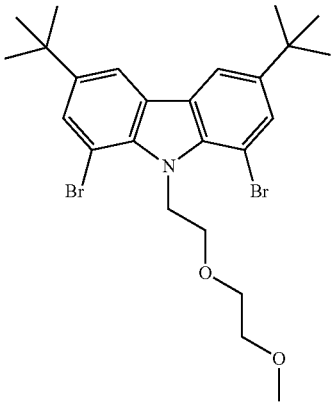

0.545 g (1.43 mmol) of VII was dissolved in 20 mL dichloromethane, along with 2.83 g (47.19 mmol) silica in a round bottom flask. The flask was covered with aluminum foil to shield its contents from light, then 0.561 g (3.15 mmol) N-bromosuccinimide was added and the flask was fitted with a rubber stopper. After 24 hours, the crude product was added to 150 mL of deionized water, extracted with 150 mL of dichloromethane, dried over $MgSO_4$, filtered to remove the drying agent, and concentrated using rotary evaporation. The crude product was purified by column chromatography on silica using a dichloromethane/hexanes gradient.

Preparation of 1-Acetyl-8-bromo-3,6-di-t-butyl-9-(diethyleneglycol monomethylether)carbazole (XII)

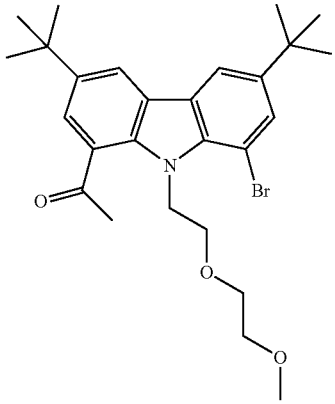

0.99 g (2.60 mmol) of VIII was dissolved in 20 mL dichloromethane, along with 5.15 g (85.8 mmol) silica in a round bottom flask. The flask was covered with aluminum foil to shield its contents from light, then 0.905 g (5.20 mmol) N-bromosuccinimide was added and the flask was fitted with a rubber stopper. After 24 hours, the crude product was added to 150 mL of deionized water, extracted with 150 mL of dichloromethane, dried over $MgSO_4$, filtered to remove the drying agent, and concentrated using rotary evaporation. The crude product was purified by column chromatography on silica using a dichloromethane/hexanes gradient.

Phenazine Calculations:

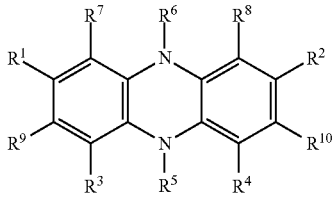

| $R^3 = R^4$ | $R^9$ | $R^1$ | $R^2$ | $R^{10}$ | $R^7 = R^8$ | $R^5 = R^6$ | E calc ($Li/Li^+$) | E exp ($Li/Li^+$) |
|---|---|---|---|---|---|---|---|---|
| H | H | H | H | H | H | $CH_3$ | 2.71 | — |
| $CH_3$ | H | H | H | H | $CH_3$ | $CH_3$ | 2.91 | — |
| t-Bu | H | H | H | H | H | $CH_3$ | 3.28 | — |
| t-Bu | H | H | H | H | t-Bu | $CH_3$ | 3.54 | — |
| t-Bu | $CF_3$ | H | H | $CF_3$ | t-Bu | $CH_3$ | 3.56 | — |
| t-Bu | $CF_3$ | H | $CF_3$ | H | t-Bu | $CH_3$ | 4.08 | — |

As set forth above, the phenazine data shows an unexpected a shift from a low oxidation potential (2.71) for a compound with no extra substituents to 2.91 for a compound with methyl substituents to 3.54 for a compound with 4 t-butyl substituents. The potential can be further increased by adding electron-withdrawing substituents at the sites not adjacent to the N atoms.

In addition, the phenothiazine data shows the unexpected effects of substituents $R^3$ and $R^4$, especially relevant for methyl and t-butyl, and also shows that the oxidation potential can be further customized by adding electron-withdrawing groups $R^1$ and $R^2$ (non-adjacent to nitrogen).

The carbazole data shows that methyl groups have a smaller steric effect (potentially due to the molecular structure of the ring system, i.e., that is, more "splayed"). However, the oxidation potential of compound II is unexpectedly over 4V, even after addition of four strongly electron-donating groups, and the oxidation is reversible, which is also unexpected.

Some examples focus on t-butyl substituents para to the N for ease of synthesis while still allowing for substitution at the 1,8 carbons (carbazole) or 1,9 carbons (phenothiazine). The observed effect is typically greater with larger groups at 1,8 (or 1,9) positions. However, substitution with trifluoromethyl or acetyl still shows a significant effect. For example, the calculated value for 3,6-di-$CF_3$-1,8-di-t-Bu-9-methylcarbazole is 4.30 V as compared to 4.13 V for 1,8-di-$CF_3$-3,6-di-t-Bu-9-methylcarbazole.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. It is contemplated that any and all values or ranges of values between those described above may also be utilized. Moreover, all combinations of all chemistries, compounds, and concepts described above, and all values of subscripts and superscripts described above, are expressly contemplated in various non-limiting embodiments. The disclosure is illustrative including words of description rather than of limitation. Many modifications and variations of the present disclosure are possible in light of the above teachings, and the disclosure may be practiced otherwise than as specifically described herein.

What is claimed is:

1. A rechargeable lithium-ion cell having a cell capacity and comprising:

A. a positive electrode having a recharged potential;

B. a negative electrode;

C. a charge-carrying electrolyte comprising a charge-carrying medium and a lithium salt; and D. a redox shuttle having the following structure:

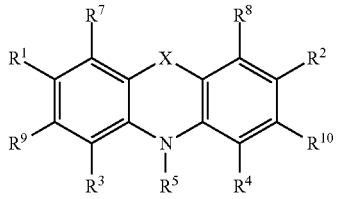

wherein X is a covalent bond, a sulfur atom (S), or N—$R^6$, and wherein each of $R^1$, $R^2$, $R^3$, $R^4$, $R^6$, $R^7$, $R^8$, $R^9$ and $R^{10}$ is independently an alkyl group, a haloalkyl group, a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, [an oxo group,] an alkyl ether group, a trialkylammoniumalkyl group, a phosphate group, a phosphonate group, or an alkyl phosphonate group, and wherein one of $R^3$ and $R^4$ is optionally a hydrogen atom; and wherein $R^5$ [is an alkyl group having 1-12 carbon atoms,] an alkylether group having 1-12 carbon atoms[,] or a trialkylammoniumalkyl group having 1-12 carbon atoms.

2. A rechargeable lithium-ion cell having a cell capacity and comprising:

A. a positive electrode having a recharged potential;

B. a negative electrode;

C. a charge-carrying electrolyte comprising a charge-carrying medium and a lithium salt; and D. a redox shuttle having the following structure:

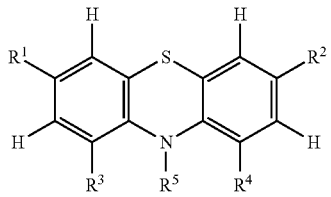

wherein each of $R^1$ and $R^2$ is independently an alkyl group, a haloalkyl group, a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, [an oxo group,] an alkyl ether group, a trialkylammoniumalkyl group, a phosphate group, a phosphonate group, or an alkyl phosphonate group;

wherein each of $R^3$ and $R^4$ is independently an alkyl group having 1 to 12 carbon atoms or a haloalkyl group having 1 to 12 carbon atoms and/or one of $R^3$ and $R^4$ is a hydrogen atom; and wherein $R^5$ is [an alkyl group having 1-12 carbon atoms, a haloalkyl group having 1-12 carbon atoms, a perhaloalkyl group having 1-12 carbon atoms,] an alkyl ether group having 1-12 carbon atoms[,] or a trialkylammoniumalkyl group having 1-12 carbon atoms.

3. The rechargeable lithium-ion cell of claim 2 wherein each of $R^1$ and $R^2$ is independently an alkyl group having 1-12 carbon atoms or a haloalkyl group having 1-12 carbon atoms.

4. The rechargeable lithium-ion cell of claim 2 wherein each of $R^1$ and $R^2$ is independently an alkyl group having 1-6 carbon atoms.

5. The rechargeable lithium-ion cell of claim 2 wherein each of $R^3$ and $R^4$ is independently an alkyl group having 1-12 carbon atoms, a haloalkyl group having 1-12 carbon atoms, a acetyl group, a haloacetyl group, or a hydrogen atom.

6. The rechargeable lithium-ion cell of claim 2 wherein each of $R^3$ and $R^4$ is independently an alkyl group having 1-6 carbon atoms.

7. The rechargeable lithium-ion cell of claim 2 wherein one of $R^3$ and $R^4$ is a hydrogen atom and the other of $R^3$ and $R^4$ is not a hydrogen atom.

8. The rechargeable lithium-ion cell of claim 2 wherein $R^5$ is [an alkyl group having 1-12 carbon atoms, an alkylether group having 1-12 carbon atoms, or] a trialkylammoniumalkyl group having 1-12 carbon atoms.

[9. The rechargeable lithium-ion cell of claim 2 wherein $R^5$ is an alkyl group having 1-6 carbon atoms.]

10. The rechargeable lithium-ion cell of claim 2 wherein said redox shuttle is dissolved in the charge-carrying electrolyte.

11. The rechargeable lithium-ion cell of claim 2 wherein said redox shuttle has an oxidation potential from 3.5 to 5 V as compared to $Li/Li^+$.

12. The rechargeable lithium-ion cell of claim 2 wherein said redox shuttle provides overcharge protection to said rechargeable lithium-ion cell after at least 10 charge-discharge cycles at a charging voltage sufficient to oxidize said redox shuttle and at an overcharge charge flow equivalent to 100% of cell capacity during each charge-discharge cycle.

13. The rechargeable lithium-ion cell of claim 2 wherein said redox shuttle provides overcharge protection to said rechargeable lithium-ion cell after at least 500 charge-discharge cycles at a charging voltage sufficient to oxidize said redox shuttle and at an overcharge charge flow equivalent to 100% of cell capacity during each charge-discharge cycle.

14. The rechargeable lithium-ion cell of claim 2 wherein said redox shuttle is present in an amount from 1 to 10 percent by weight based on a total weight of said charge-carrying electrolyte.

15. The rechargeable lithium-ion cell of claim 2 wherein said positive electrode comprises $LiFePO_4$, $Li_2FeSiO_4$, $MnO_2$, $Li_xMnO_2$, $LiNiMnCoO_2$, and/or $LiNiCoAlO_2$, wherein x is 0.3 to 0.4.

16. The rechargeable lithium-ion cell of claim 2 wherein said negative electrode comprises graphitic carbon, lithium metal or a lithium alloy.

17. The rechargeable lithium-ion cell of claim 2 wherein said charge carrying medium comprises ethylene carbonate, propylene carbonate, dimethyl carbonate, diethyl carbonate, ethylmethyl carbonate or combinations thereof.

18. A rechargeable lithium-ion cell having a cell capacity and comprising:

A. a positive electrode having a recharged potential;

B. a negative electrode;

C. a charge-carrying electrolyte comprising a charge-carrying medium and a lithium salt; and D. a redox shuttle having the following structure:

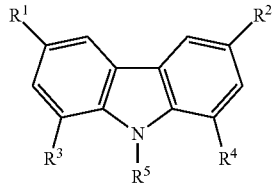

wherein each of $R^1$ and $R^2$ is independently an alkyl group, a haloalkyl group, a perhaloalkyl group, or an alkyl ether group;

*wherein each of $R^3$ and $R^4$ is independently an alkyl group, a haloalkyl group, a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, an alkyl ether group, a trialkylammoniumalkyl group, a phosphate group, a phosphonate group, or an alkyl phosphonate group;* wherein at least one of $R^3$ and $R^4$ is an alkyl group, a haloalkyl group, a perhaloalkyl group, an alkyl ether group, an acyl group, or a haloacyl group; and wherein $R^5$ is [an alkyl group,] an alkyl ether group[.] *or* a trialkylammoniumalkyl group[, an acetyl group, or a $CF_3$ group].

19. An article comprising the rechargeable lithium-ion cell of claim 2.

20. An array comprising two or more of said rechargeable lithium-ion cells of claim 2.

21. The rechargeable lithium-ion cell of claim 18 wherein each of $R^1$ and $R^2$ is independently an alkyl group having 1-12 carbon atoms.

22. The rechargeable lithium-ion cell of claim 18 wherein each of $R^3$ and $R^4$ is independently an alkyl group having 1-6 carbon atoms or a haloalkyl group having 1-12 carbon atoms.

23. The rechargeable lithium-ion cell of claim 18 wherein said redox shuttle has an oxidation potential from 3.5 to 5 V as compared to $Li/Li^+$.

24. An article comprising the rechargeable lithium-ion cell of claim 18.

25. An array comprising two or more of said rechargeable lithium-ion cells of claim 18.

* * * * *